(12) United States Patent
Maia Cavali

(10) Patent No.: US 11,382,669 B2
(45) Date of Patent: Jul. 12, 2022

(54) GUIDE DEVICE FOR ATTACHMENT AND TRANSFIXATION OF SLIDING PLATES FOR DYNAMIC IMPLANTS

(71) Applicant: Paulo Tadeu Maia Cavali, Sao Paulo (BR)

(72) Inventor: Paulo Tadeu Maia Cavali, Sao Paulo (BR)

(*) Notice: Subject to any disclaimer, the term of this patent is extended or adjusted under 35 U.S.C. 154(b) by 12 days.

(21) Appl. No.: 16/758,912

(22) PCT Filed: Oct. 24, 2017

(86) PCT No.: PCT/BR2017/000128
§ 371 (c)(1),
(2) Date: Apr. 24, 2020

(87) PCT Pub. No.: WO2019/079863
PCT Pub. Date: May 2, 2019

(65) Prior Publication Data
US 2021/0177467 A1    Jun. 17, 2021

(51) Int. Cl.
*A61B 17/70*    (2006.01)

(52) U.S. Cl.
CPC ........ *A61B 17/7046* (2013.01); *A61B 17/701* (2013.01); *A61B 17/7014* (2013.01); *A61B 17/7031* (2013.01); *A61B 17/7083* (2013.01)

(58) Field of Classification Search
CPC .............. A61B 17/701; A61B 17/7014; A61B 17/7031; A61B 17/7046; A61B 17/7083
See application file for complete search history.

(56) References Cited

U.S. PATENT DOCUMENTS

| | | | | |
|---|---|---|---|---|
| 2009/0062864 A1* | 3/2009 | Ludwig | ............... | A61B 17/7041 606/301 |
| 2009/0270916 A1* | 10/2009 | Ramsay | ............. | A61B 17/1735 606/246 |
| 2010/0168796 A1* | 7/2010 | Eliasen | ............... | A61B 17/7035 606/264 |

(Continued)

FOREIGN PATENT DOCUMENTS

| | | |
|---|---|---|
| BR | PI0706247 A2 | 12/2009 |
| EP | 0669108 A2 | 8/1995 |

(Continued)

OTHER PUBLICATIONS

International Search Report, Institute Nacional Da Propriedade Industrial, dated Feb. 19, 2018.

(Continued)

*Primary Examiner* — Nicholas J Plionis
(74) *Attorney, Agent, or Firm* — Bay State IP, LLC

(57) ABSTRACT

A guiding device for fixing flexible blades of spinal implants, which includes a guide device for transfixing flexible blades (1) that constitute the platforms (13) and (14), which have a box-shaped side, where the set of flexible blades (3) crosses and slides, and the other side has a hole (16) for its fixation to the double intermediate connector (5), which bears a pedicle screw (7); said set of flexible blades (3) being formed by two blades (4), overlapped, provided with longitudinal openings (9), through which they are joined by means of a fixing device (11), which allow them to slide over each other.

4 Claims, 6 Drawing Sheets

(56) References Cited

U.S. PATENT DOCUMENTS

Figure 1:
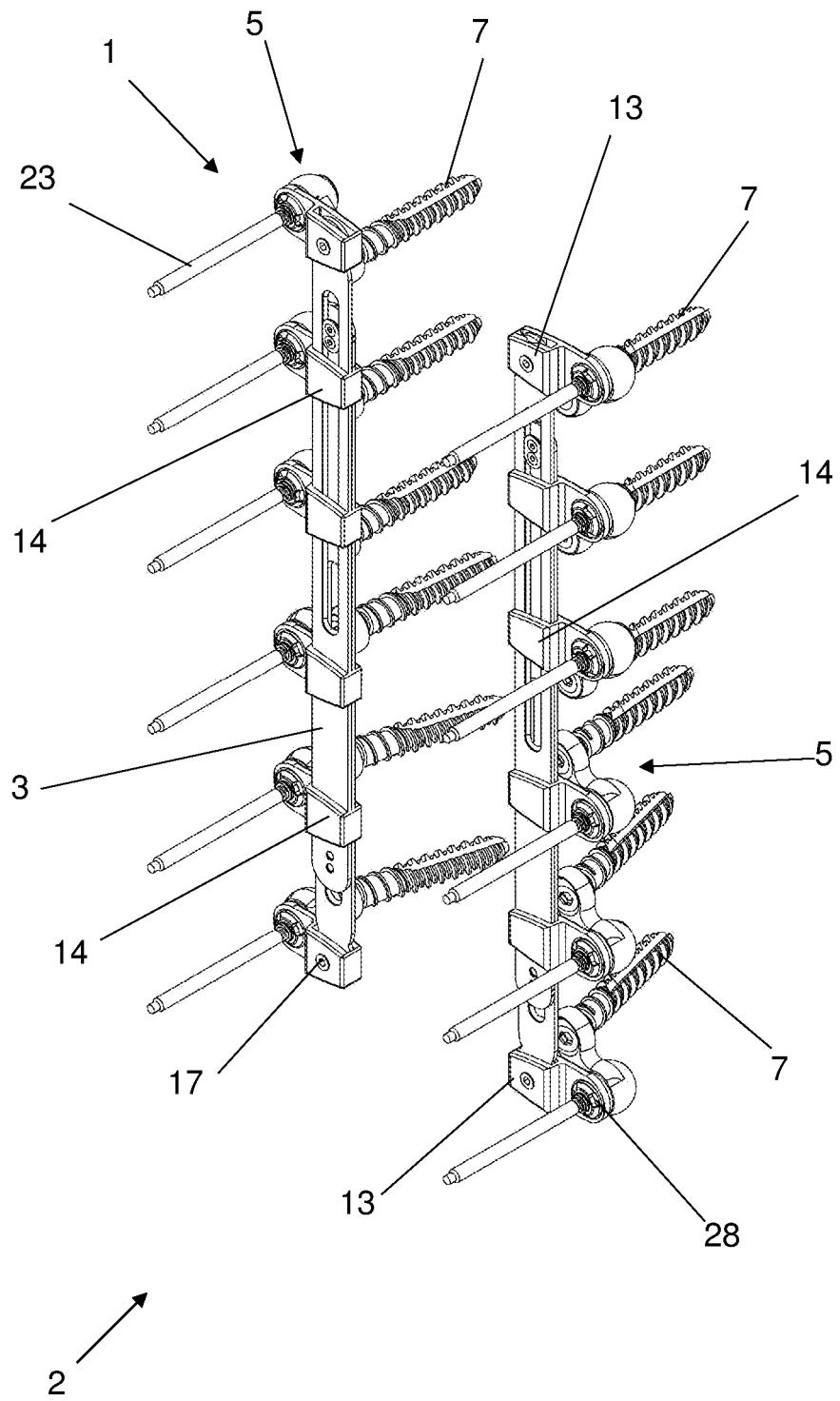

2011/0245877 A1* 10/2011 Pisharodi ........... A61B 17/7037
606/268
2011/0270314 A1* 11/2011 Mueller ............... A61B 17/704
606/264

FOREIGN PATENT DOCUMENTS

WO      2005046515 A2    5/2005
WO      2010030906 A1    3/2010

OTHER PUBLICATIONS

Written Opinion of the International Searching Authority, Instituto Nacional Da Propriedade Industrial, dated Feb. 19, 2018.

* cited by examiner

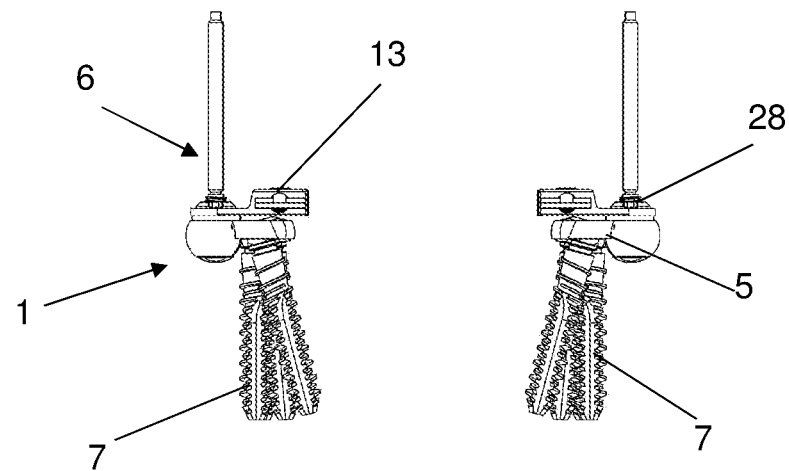
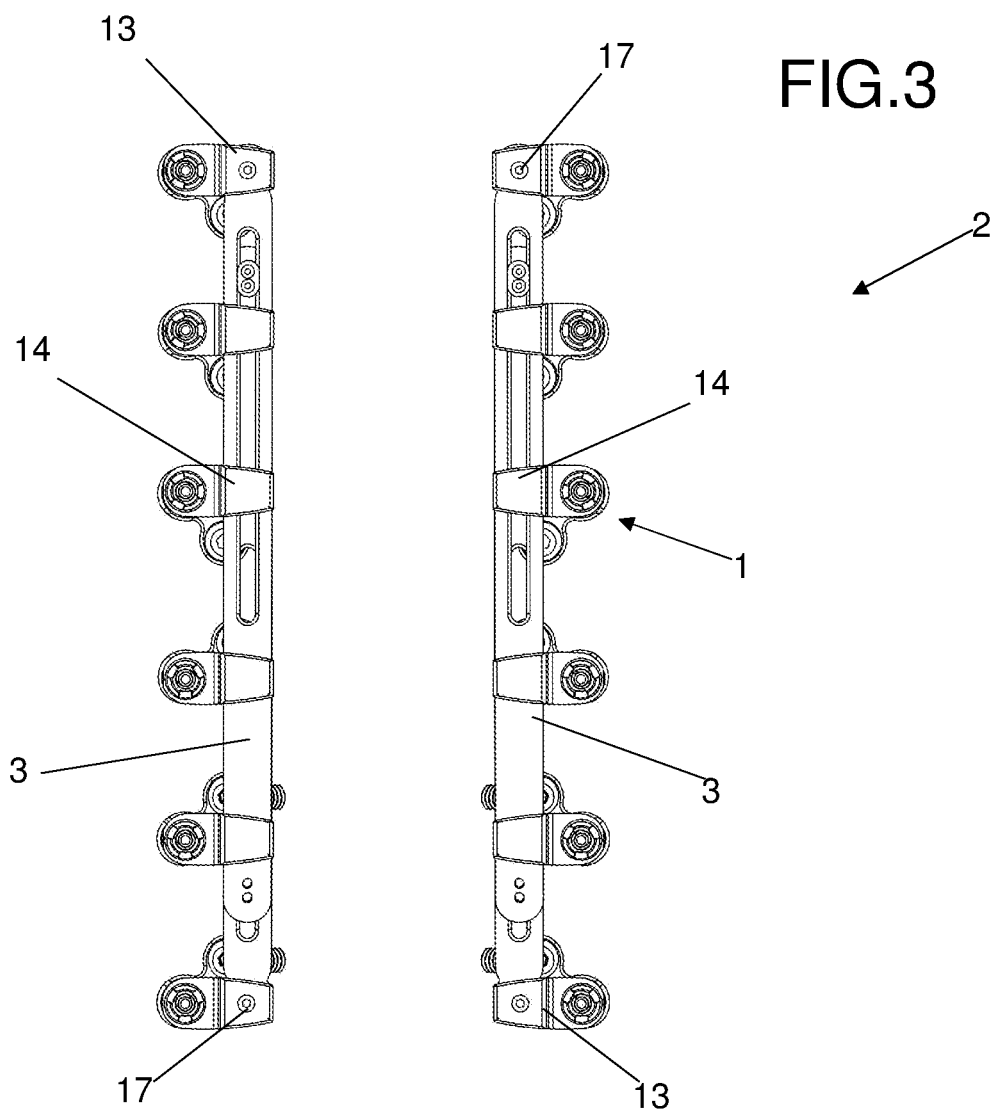

GUIDE DEVICE FOR ATTACHMENT AND TRANSFIXATION OF SLIDING PLATES FOR DYNAMIC IMPLANTS

CROSS REFERENCE TO RELATED APPLICATION

This application is for entry into the U.S. National Phase under § 371 for International Application No. PCT/BR2017/000128 having an international filing date of Oct. 24, 2017, and from which priority is claimed under all applicable sections of Title 35 of the United States Code including, but not limited to, Sections 120, 363, and 365(c).

FIELD OF THE INVENTION

The present invention patent relates to a guiding device for fixing flexible, sliding and dynamic blades for selective stabilization and correction of spinal deformities and instabilities, pertaining to the medical science area, more specifically the field of surgical items for the treatment of bones or joints and devices specially adapted to them.

The object of the present application was developed in an attempt to assist in the rehabilitation of the spine in cases of fractures, vertebral deformities, degenerative diseases, spinal tumors, among other typical problems, while allowing the patient to maintain assisted spine mobility with greater comfort during their rehabilitation or in a definitive capacity.

This is, therefore, a guiding device for fixing flexible blades and components that enable the placement of pedicle screws, which fix said blades on the vertebrae, at various angles, in addition to displacing their fixation point on the flexible blade. In this way, even after implantation, it is possible to move the fixation point on the blade without the need to change the fixation point on the spine's vertebrae.

STATE OF THE ART

The implants known in the state of the art that assist in the rehabilitation of the spine in cases of fractures, vertebral deformities, degenerative diseases, spinal tumors, among other typical problems, basically comprise a rod, fixed to each vertebra or set of vertebrae rigidly by means of pedicle screws, in such a way that, after correction of the deformity, the spine remains aligned according to the pre-modeling and positioning of the rigid rods.

POINTS OF CONCERN IN THE STATE OF THE ART

The disadvantage of the traditional implant is that the segment of the operated spine may lose its mobility and natural flexibility, thus limiting the movements of the patient's torso and, as a consequence of this loss of mobility, in the medium and long term, the vertebral segments adjacent to the fixation undergo degeneration of the intervertebral discs and facet joints, causing early osteoarthritis, spinal pain and enormous discomfort.

Another important drawback of the traditional spinal implant procedure refers to the loss of growth and spinal development in the spines of immature (developing) patients.

In addition to allowing the movements of the spine in the planes that are not blocked by the system and allowing the growth of the immature spine (undergoing growth); this new system of flexible implants can be applied to the spine without the destruction or removal of the anatomical structures of the spine such as intraspinal ligaments, supraspinous ligaments, yellow ligament, spinous processes and interfacetary joints, that is, these implants are implanted and maintain the vertebral structures of the operated segment intact.

SUMMARY OF THE INVENTION

In order to solve these issues, the inventor, a person with experience in the area, created and developed the object "GUIDE DEVICE FOR FIXING AND TRANSFIXING SLIDING BLADES FOR DYNAMIC IMPLANTS" for the selective stabilization and correction of spinal deformities and instabilities.

The innovation refers to a project that includes a set of fixation heads for flexible blades.

Said flexible blade set consists of two overlapping blades that slide one over the other, in order to be retracted or extended as needed.

Said blade set is affixed to the patient's spine by means of multiple pedicle screws with a guide device for transfixing the blades that are positioned at the ends and along their extension and implanted at specific points in the respective vertebrae.

The innovation refers to the system for fixing the blade assembly to the spine, comprising a head that consists of a double bearing mounted on a sliding support, which enables the placement of the pedicle screw at various angles, in addition to displacing its fixation point in the flexible blade. In this way, even after implantation, it is possible to move the fixation point on the blade without the need to change the fixation point on the spine's vertebrae.

For the execution of the new flexible implant technique, the innovation is understood as a project that includes four parts or types of implantable components.

Part 1: Pedicle screw.

Fixation (anchoring) implants attached to the vertebra by means of pedicle screws, whose heads are characterized by remaining only three or four millimeters outside of the bone surface and by having a central hole to receive a small screw that will fix the double intermediate connector that fits into the head of the pedicle screw.

Part 2: Double intermediate connector.

This double intermediate connector is boomerang shaped and has two sides. One side has the socket for the pedicle screw and the other side has a polyaxial threaded rod to be attached to the blade platform.

Part 3: Blade platform.

The blade platforms have a rail through which the set of flexible and sliding blades will pass. These platforms have two sides. One box-shaped side where the set of flexible blades will pass and slide and the other side having a hole for fixation with the double intermediate connector.

For each vertebra, two platforms of blades are provided anchored to each vertebral pedicle, that is, one platform connected to the right pedicle and another connected to the left pedicle of the same vertebra.

As such, the segment operated on the right side will present the platforms with a set of flexible sliding blades, and on the left side another set of blades passing through the platforms connected to the pedicles on the left side.

On each side of the assembled system, we will have a terminal platform at each end and multiple sliding platforms according to the spinal segment operated.

Part 4: Sliding blades.

These implants are a set of two or more flexible blades, which slide between themselves and within the platforms.

Such sets of blades are mounted on both sides of the operated spine, that is, right and left next to the spinous processes, in such a way that, for each side of the spine, at least one set of two sliding blades is connected to the platforms, which, in turn, are connected to pedicle screws.

Assembly Characteristics

At each side of the vertebral segment equipped with the system, we will have:

A blade attached only at one end to the proximal terminal platform that is attached to the proximal terminal vertebra.

The other blade is also attached only at one end to the distal end platform, which is attached to the distal end vertebra.

In each system, each blade is fixed only at one end so that they can slide together. Thus the inner edges of the blades are free to slide between themselves and run loose within the sliding platforms.

The important thing is that the set of sliding blades allow the shortening and elongation of the operated vertebral segment and, also due to the flexibility, it is important that they allow the angular movements of flexion, extension and rotation of the operated vertebral segment.

With the assembly of the system, the set of flexible and sliding blades that slide and run inside the sliding platforms, which in turn are anchored to the pedicle screws through the double intermediate connectors, allows for the correction of vertebral deformities such as scoliosis, maintains the movements of the spine in the free planes allowed by the system and allows spine growth when applied to an immature patient (children and adolescents).

This system can be applied by modulating and partially blocking the sliding between the blades for the treatment of kyphosis, vertebral fractures, tumors and instabilities caused by degenerative spine disease.

Thus, the present patent was designed to obtain a prosthesis with as few parts as possible, conveniently configured and arranged to allow the flexible, sliding and dynamic implant system to perform selective stabilization and correct spinal deformities and instabilities, performing its functions with unmatched efficiency and versatility, without the aforementioned drawbacks.

BRIEF DESCRIPTION OF THE INVENTION DRAWINGS

In order to provide a better understanding of what constitutes the "GUIDE DEVICE FOR FIXING AND TRANSFIXING SLIDING BLADES FOR DYNAMIC IMPLANTS", claimed herein, the accompanying illustrative drawings are presented, where one may see:

FIG. 1—A side perspective view of two flexible, sliding and dynamic implants for selective stabilization and correction of spinal deformities and instabilities, one left and one right.

FIG. 2—A bottom view of two flexible, sliding and dynamic implants for selective stabilization and correction of spinal deformities and instabilities, one left and one right.

FIG. 3—A front view of two flexible, sliding and dynamic implants for selective stabilization and correction of spinal deformities and instabilities, one left and one right.

Figure 4:
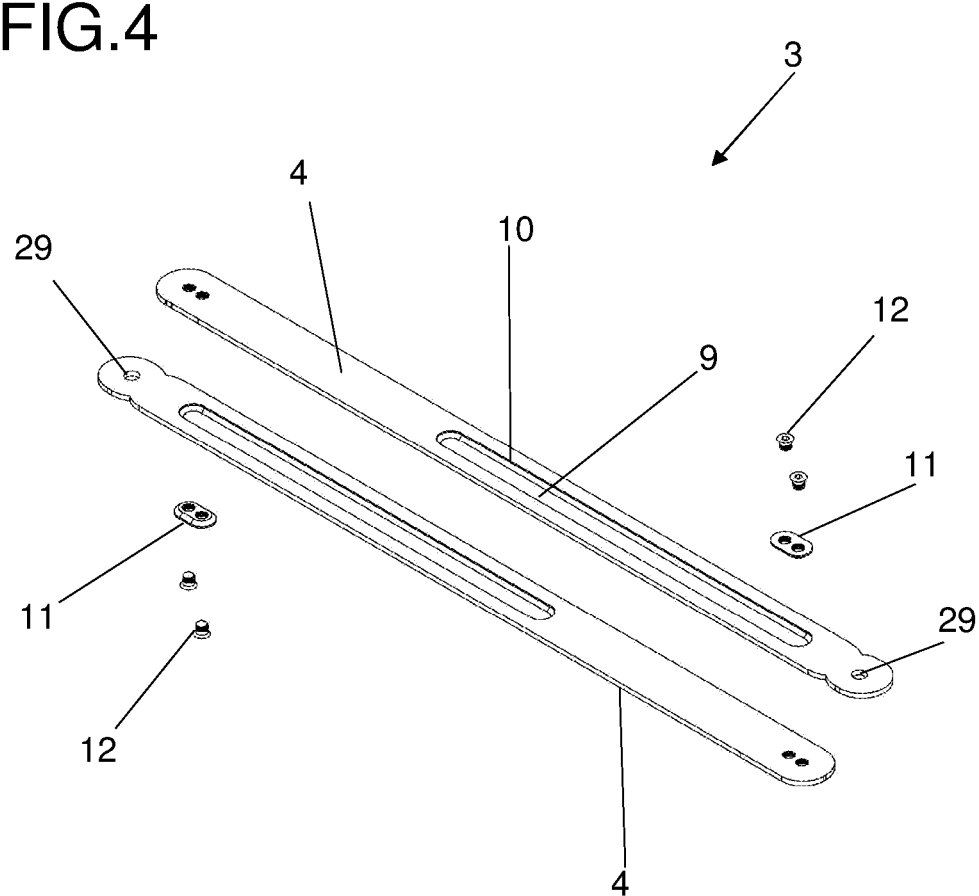

FIG. 4—An exploded perspective view of the straight, sliding rod that comprises the flexible, sliding and dynamic implant for selective stabilization and correction of spinal deformities and instabilities.

Figure 5:
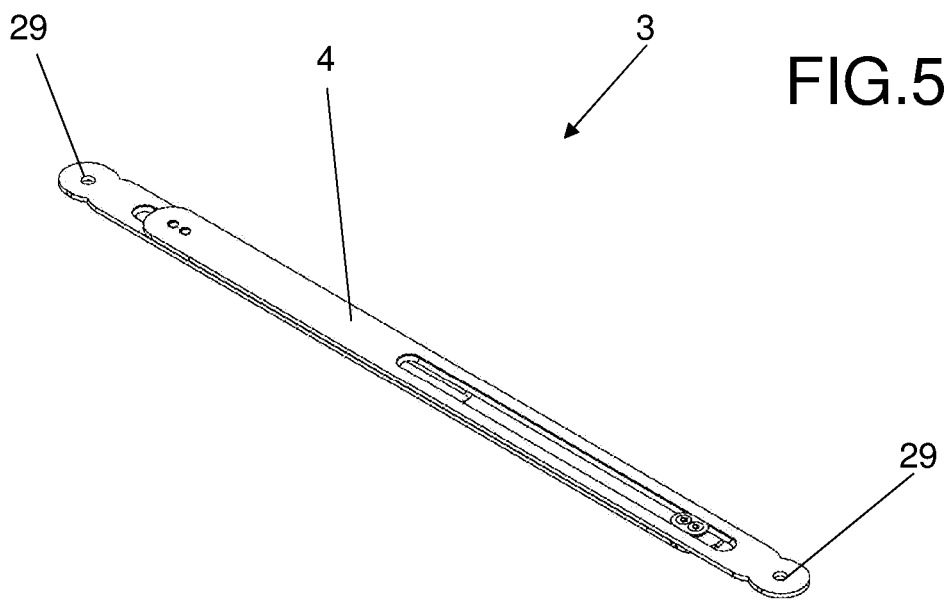

FIG. 5—A perspective view of the straight, sliding rod that comprises the flexible, sliding and dynamic implant for selective stabilization and correction of spinal deformities and instabilities.

Figure 6:
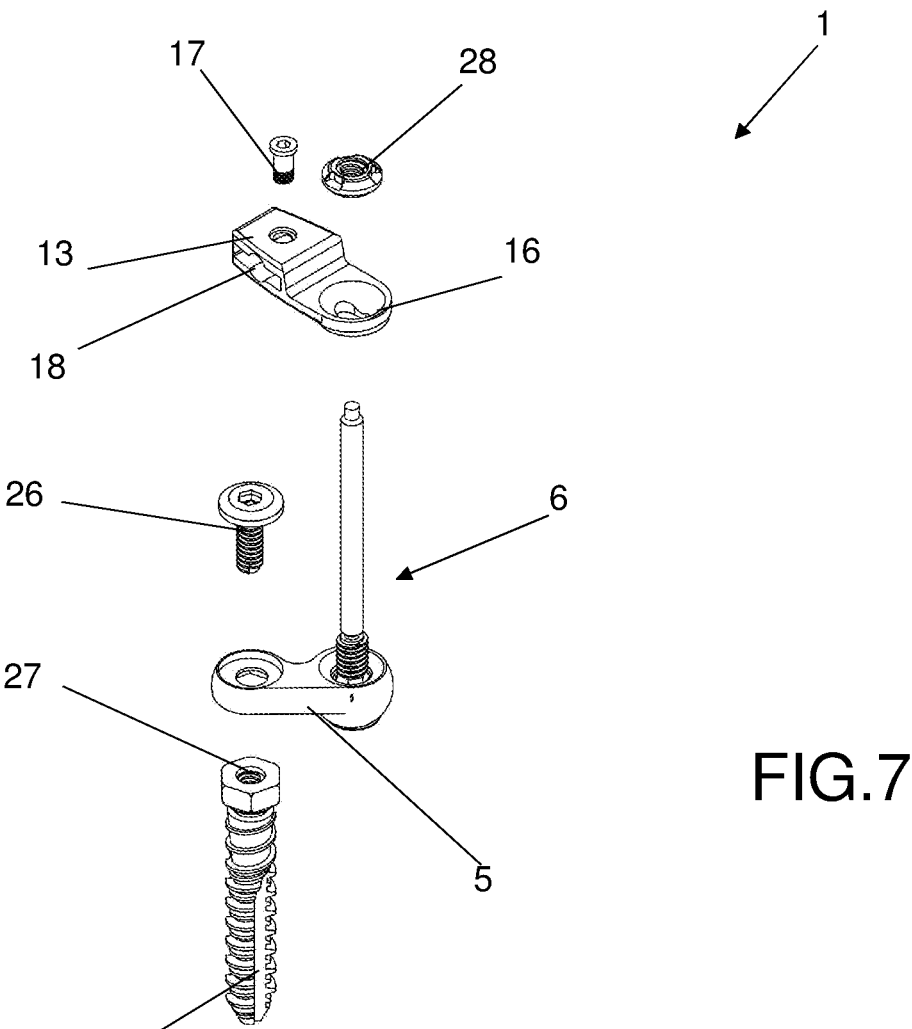

FIG. 6—An exploded view of the set formed by the terminal support, the ball joint, the double bearing and the pedicle screw.

Figure 7:
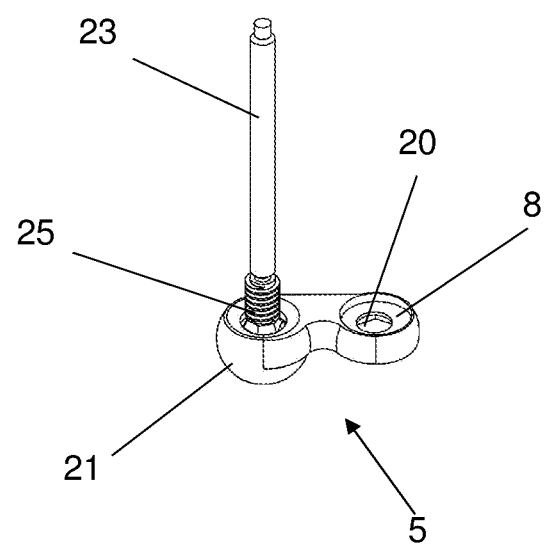

FIG. 7—A perspective view of the double bearing with the ball joint.

Figure 8:
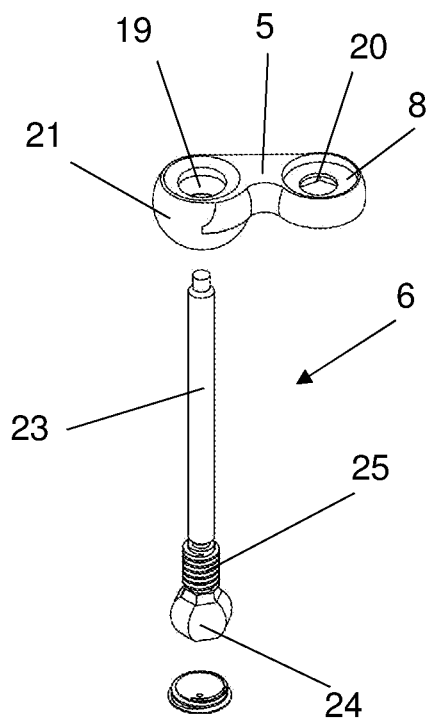

FIG. 8—An exploded perspective view of the double bearing with the ball joint.

Figure 9:
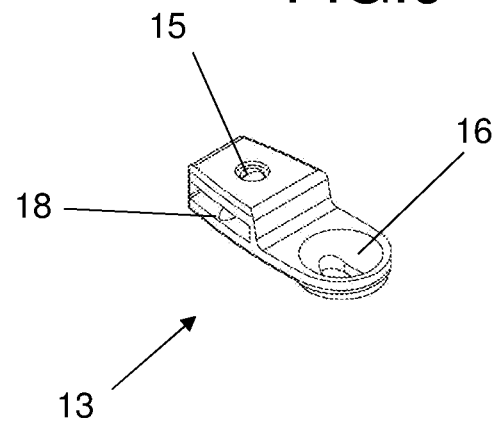

FIG. 9—A rear perspective view of the terminal support.

Figure 10:
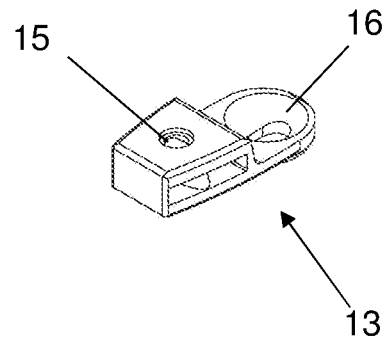

FIG. 10—A front perspective view of the terminal support.

Figure 11:
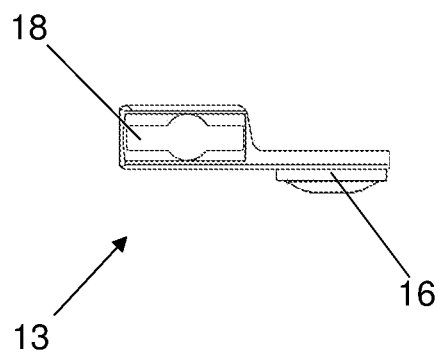

FIG. 11—A front view of the terminal support.

Figure 12:
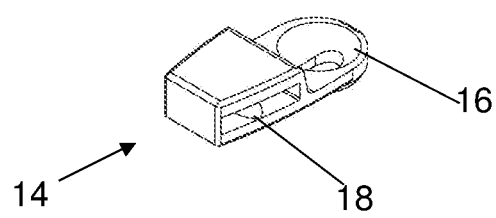

FIG. 12—A front perspective view of the sliding support.

Figure 13:
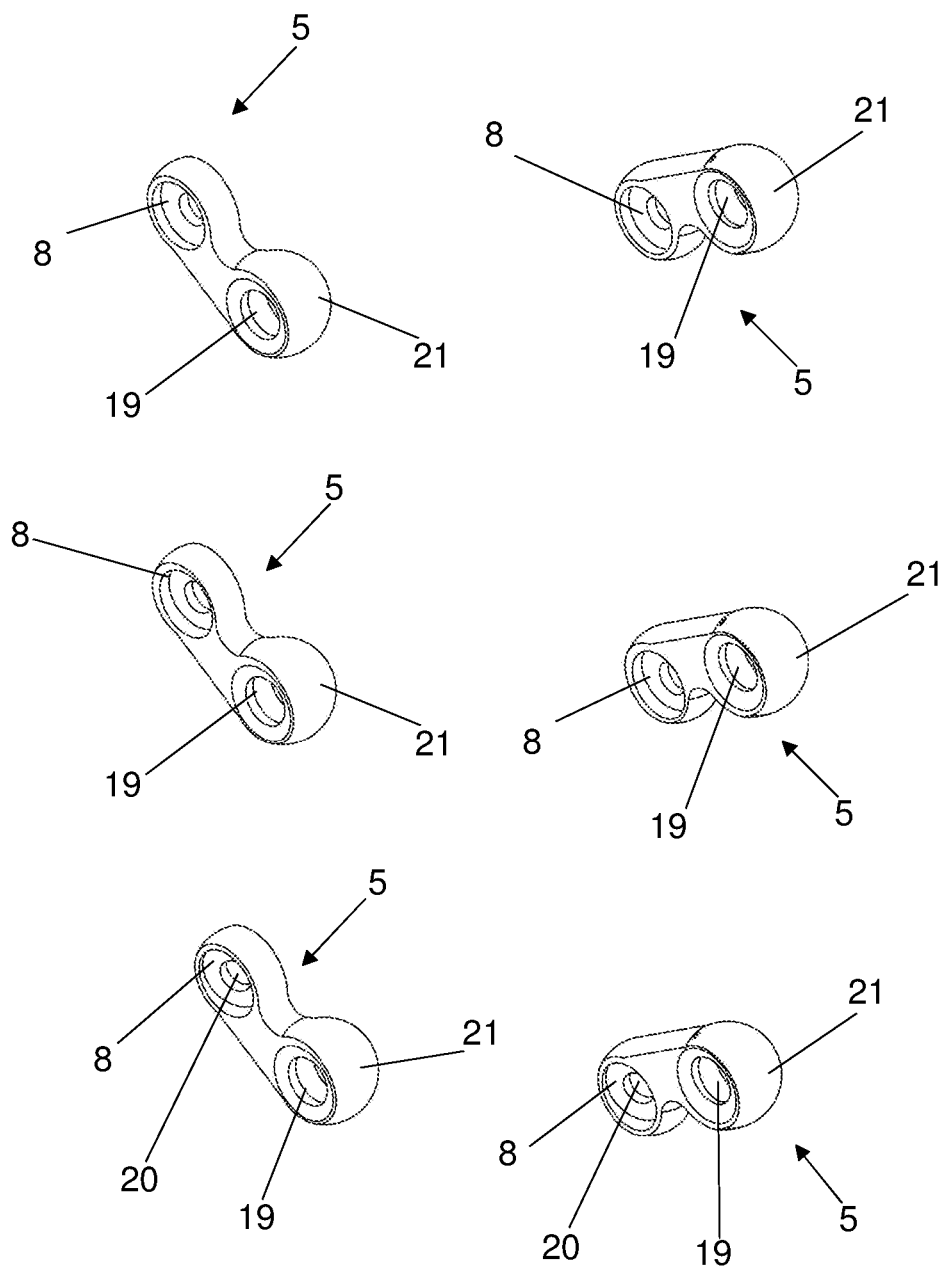

FIG. 13—A perspective view of the set of double bearings that integrate the implant system in question, where one may see, from top to bottom, in the left column: the double lumbar bearing, whose pedicle screw projects in the perpendicular direction; the lumbar bearing whose screw protrudes five degrees; and the lumbar bearing whose screw protrudes fifteen degrees. In the right column: the thorax bearing whose screw projects in the perpendicular direction; the thorax bearing whose screw protrudes five degrees and the double thorax bearing whose screw protrudes fifteen degrees.

DETAILED DESCRIPTION OF THE INVENTION

In accordance with the figures above, the "GUIDE DEVICE FOR FIXING AND TRANSFIXING SLIDING BLADES FOR DYNAMIC IMPLANTS", the object of this patent, consists of a guide device for transfixing flexible blades (1), for postural correction and/or spine treatment comprising all degrees of natural mobility equivalent to a healthy spine.

Said flexible blades (4) integrate an articulated vertebral prosthesis (2) consisting of two sets of blades (3), which are mounted on both sides of the operated spine.

Said set of blades (3) comprises two overlapping thin blades (4), which can be slid longitudinally over each other and are positioned on the rails of two end platforms (13) and multiple sliding platforms (14), whereas each end is fixed to the respective terminal platform (13) through screws (17).

Said terminal platforms (13) and slides (14) integrate a guide device for transfixing flexible blades (1), which also comprise double intermediate connectors (5) shaped like a boomerang, which have polyaxial threaded rods (6) and pedicle screws (7).

Said pedicle screws (7) are attached to the bone region of each vertebra, relative to the vertebral extension to be implanted, of the patient, and the polyaxial threaded rods (6) project to the opposite side in relation to the pedicle screws (7). Said pedicle screw (7) is outside the bone surface and has a central hole (27), which receives a small screw (26), which fixes the double intermediate connector (5), which fits in the head of said pedicle screw (7).

More specifically, the set of blades (3) consists of two identical, thin, rigid blades (4), of elongated geometry and with rounded edges, i.e. without sharp edges and with an oblong longitudinal opening (9) that occupies approximately half of its length, with a tilted edge (10).

Said blades (4) are overlapped and joined by means of two fasteners (11) that are fitted in each longitudinal opening (9)

provided for in the blades (4) and affixed to the ends of the other blade (4), using screws (12).

Said fasteners (11) are flat rectangular elements, with rounded smaller sides, which fit into the inclined edges (10) of the longitudinal openings (9) and allow the blades (4) to slide longitudinally with each other. There are also two through-holes with a truncated conical profile aligned longitudinally in the median line of the said fastener (11).

Two terminal platforms (13) are attached to the set of blades (3), one at each end and multiple sliding platforms (14) along its length.

Said terminal platform (13) is constituted by a hollow quadrangular element and open in the whole of its lower and upper face, provided with a threaded circular hole (15) in its upper face and with a hole (16) that protrudes from the left side.

At each end of the rectilinear structure, a terminal platform (13) is attached by means of a screw (17) inserted and threaded into the threaded circular hole (15), which passes through a circular hole (29), provided in that region of the blade (4), and contacts the bottom face of the terminal platform (13).

The sliding platform (14) has the same conformation as the terminal platform (13), but without the threaded circular hole, i.e. it consists of a hollow quadrangular element and opened in the whole of its lower and upper face, in the form of a box comprising a track (18) where the set of flexible blades (3) passes and slides, and on the opposite side there is a hole (16), for attachment to the double intermediate connector.

Said sliding platforms (14) are coupled to the set of blades (3) and are positioned along its length in positions coincident with the respective vertebrae to which the pedicle screws will be attached.

Each platform (13) and (14) receives a double intermediate connector (5) comprised of a monoblock piece, in the form of a boomerang, equipped with two through holes (19) and (20), the hole (19) being flanked by higher walls (21), where a polyaxial threaded rod (6) is coupled, which consists of a cylindrical rod (23), whose lower end has a sphere (24) preceded by a threaded region (25). The other hole (20) receives a pedicle screw (7) on one side and a fixing screw (26) on the other, which is threaded into the concentric hole (27) in the head of the pedicle screw (7), in order to attach it against an internal flange (8) provided in the hole (20). Said internal flange (8) is responsible for orienting the angle of the pedicle screw (7) and, therefore, several double intermediate connectors (5) are provided, whose internal flange angles (8) vary for the different positions they occupy in the set of blades (3).

The cylindrical rod (23) of the threaded polyaxial rod (6) is passed through the hole (19) of the double intermediate connector (5) and hole (16) of the platform (13) or (14) and fixed by means of a nut (28) which is threaded in the threaded region (25).

One may see that the internal flanges (8) of the double intermediate connectors (5) have different angles, so that the respective pedicle screws (7) are at suitable angles for attaching the implant to the respective vertebra and, therefore, each type of double intermediate connector (5) has a specific position.

The upper terminal platform (13) is affixed to the first corresponding upper vertebra of the vertebral extension to be implanted and the lower terminal platform (13) is affixed to the last lower vertebra of that extension and the sliding platforms (14) are affixed to the vertebrae contained within said range.

These implants are a set of two or more flexible blades, which slide between themselves and within the platforms.

It is certain that, when this invention is put into practice, modifications may be introduced regarding certain construction and form details, without that fact implying a departure from the fundamental principles that are clearly substantiated in the claim framework, with it thus being understood that the terminology employed was chosen for the purpose of description and not limitation.

The invention claimed is:

1. A guide device configured to transfix flexible blades (1) for postural correction and/or spine treatment, characterized in that it consists of a plurality of terminal platforms (13, 14), wherein each terminal platform receives a double intermediate connector (5) which includes a single piece with two halves, equipped with two through holes (19, 20), the hole (19) being flanked by walls (21) of the double intermediate connector (5) that are higher than walls of the double intermediate connector (5) that flank the hole (20), where a polyaxial threaded rod (6) is coupled with the hole (19), wherein the polyaxial threaded rod (6) consists of a cylindrical rod (23), whose lower end has a sphere (24) preceded by a threaded region (25), with the other hole (20) receiving a pedicle screw (7) on one side and a fixing screw (26) on the other, wherein the fixing screw (26) is threaded into a concentric hole (27) in a head of the pedicle screw (7), so as to fix the fixing screw (26) against an internal flange (8) provided in the hole (20), said internal flange (8) being responsible for orienting the angle of the pedicle screw (7) and therefore a plurality of double intermediate connectors (5) are provided, whose internal flange angles (8) vary for the different positions they occupy in a blade set (3).

2. A guide device configured to transfix flexible blades (1) for postural correction and/or spine treatment according to claim 1, characterized in that said terminal platforms (13, 14) are configured to keep vertebral structures of a segment intact.

3. A guide device configured to transfix flexible blades (1) for postural correction and/or spine treatment according to claim 1, characterized in that each polyaxial threaded rod (6) is configured to attach to a blade platform (4).

4. A guide device configured to transfix flexible blades (1) for postural correction and/or spine treatment according to claim 1, characterized in that the terminal platforms (13, 14) of the blades have a rail (18) where the blade set (3) will slide, whereas the terminal platforms (13, 14) have two sides, one side in a box shape where the blade set (3) will pass and slide and the other side has a hole (16) for attachment to a respective double intermediate connector (5).

* * * * *